United States Patent [19]
Stark et al.

[11] Patent Number: 6,116,736
[45] Date of Patent: Sep. 12, 2000

[54] PUPILOMETER WITH PUPIL IRREGULARITY DETECTION CAPABILITY

[75] Inventors: Lawrence W. Stark; Claudio M. Privitera, both of Berkeley; Kamran Siminou, Newport Beach, all of Calif.; Jeffrey Oliver, Cedar Park, Tex.

[73] Assignee: Neuroptics, Inc., Newport Beach, Calif.

[21] Appl. No.: 09/298,670

[22] Filed: Apr. 23, 1999

[51] Int. Cl.$^7$ ........................................... A61B 3/14
[52] U.S. Cl. ................................................. 351/206
[58] Field of Search .............................. 351/204, 206, 351/210, 211, 212, 246

[56] References Cited

U.S. PATENT DOCUMENTS

| | | | |
|---|---|---|---|
| Re. 28,873 | 6/1976 | Morgan | 128/249 |
| 3,533,683 | 10/1970 | Stark et al. | 351/1 |
| 3,533,684 | 10/1970 | Stark et al. | 351/1 |
| 3,638,640 | 2/1972 | Shaw | 128/2 |
| 4,157,864 | 6/1979 | Koller et al. | 351/160 |
| 4,194,815 | 3/1980 | Trombley | 351/160 |
| 4,410,245 | 10/1983 | Koester | 351/219 |
| 4,485,820 | 12/1984 | Flower | 128/633 |
| 4,649,908 | 3/1987 | Ghaly | 128/132 |
| 4,652,099 | 3/1987 | Lichtman | 351/162 |
| 4,664,490 | 5/1987 | Rol | 351/219 |
| 4,755,043 | 7/1988 | Carter | 351/219 |
| 4,863,260 | 9/1989 | Gersten et al. | 351/212 |
| 4,871,247 | 10/1989 | Haynes | 351/219 |
| 4,907,597 | 3/1990 | Chamoun | 128/731 |
| 4,907,872 | 3/1990 | Schirmer et al. | 351/160 |
| 4,966,452 | 10/1990 | Shields et al. | 351/219 |
| 5,010,891 | 4/1991 | Chamoun | 128/731 |
| 5,117,835 | 6/1992 | Mick | 128/748 |
| 5,179,953 | 1/1993 | Kursar | 128/645 |
| 5,187,506 | 2/1993 | Carter | 351/221 |
| 5,214,456 | 5/1993 | Gersten | 352/212 |
| 5,336,215 | 8/1994 | Hsueh et al. | 606/4 |
| 5,408,998 | 4/1995 | Mersch | 128/633 |
| 5,543,865 | 8/1996 | Nanjo | 351/206 |
| 5,646,709 | 7/1997 | Carter | 351/218 |

OTHER PUBLICATIONS

L. Stark, et al., Pupil Unrest: An Example of Noise in a Biological Servomechanism, *Nature*, 4639, pp. 857–858, Sep. 27, 1958.

L. Stark, Stability, Oscillations, and Noise in the Human Pupil Servomechanism, *Proceedings of the IRE*, pp. 1925–1939, 1959.

S. Asano, et al., Pupillometry, *Quarterly Progress Report No. 66, Mass. Inst. of Technology*, pp. 404–412, Jul. 15, 1962.

C.A. Finnila, *A Convenient Eye Position and Pupil Size Meter* (partial), 4 pages, 1960.

A. Yarbus, *Eye Movements and Vision*, Plenum Press, N.Y., pp. 28–41, 1967.

Usui, et al., Sensory and Motor Mechanisms Interact To Control Amplitude of Pupil Noise, *Vision Res.*, vol. 18, pp. 505–507, 1978.

Marshall, et al., The Oval Pupil: Clinical Significance and Relationship To Intracranial Hypertension, *J. Neurosurg*, vol. 58, pp. 566–568, Apr. 1983.

(List continued on next page.)

*Primary Examiner*—George Manuel
*Attorney, Agent, or Firm*—Lyon Lyon LLP

[57] ABSTRACT

A pupilometer having a pupil irregularity or non-uniformity detection capability. The pupilometer may comprise an imaging sensor for generating signals representative of a pupil of an eye, a data processor; and a program executable by the data processor for enabling the data processor to process signals received from the imaging sensor and to thereby identify one or more regions of non-uniformity within an image of a perimeter of the pupil. The pupilometer may incorporate several innovative calibration and thresholding routines and may provide the basis for an innovative medical diagnostics system, when coupled to a network containing a suitable medical database and data processing hardware.

41 Claims, 10 Drawing Sheets

OTHER PUBLICATIONS

Sun, et al., Pupillary Escape Intensified By Large Pupillary Size, *Vision Res.*, vol. 23, No. 6, pp. 611–615, 1983.

Stark, The Pupil As A Paradigm For Neurological Control Systems, *IEEE Transactions On Biomedical Engineering*, vol. BME–31, No. 12, pp. 919–923, Dec. 1984.

Krenz, et al., Neurophysiological Model Of The Normal And Abnormal Human Pupil, *IEEE Transactions On Biomedical Engineering*, vol. BME–32, No. 10, pp. 817–825, Oct. 1985.

Marshall, et al., Pupillary Abnormalities, Elevated Intracranial Pressure And Mass Lesion Location, *Intracranial Pressure VI*, Springer–Verlag Berlin Heidelberg, pp. 656–660, 1986.

Stark, et al., Instrumentation And Robotic Image Processing Using Top–Down Model Control, *Robotics and Manufacturing*, ASME Press, 675–682, 1988.

Bishop, Pathologic Pupillary Signs: Self–Learning Module, Part 1, *Critical Care Nurse*, vol. 11, No. 6, pp. 58–63.

Bishop, Pathologic Pupillary Signs: Self–Learning Module, Part 2, *Critical Care Nurse*, vol. 11, No. 7, pp. 58–67.

Bishop, Pathologic Pupillary Signs: Self–Learning Module, Part 3, *Critical Care Nurse*, vol. 11, No. 8, pp. 30–32.

Stark, The Pupil As A Paradigm Example A Neurological Control System: Mathematical Approaches in Biology, *The Pupil: Anatomy, Physiology, and Clinical Applications*, vol. I, Iowa State University Press, pp. 630–647, 1993.

Myers, et al., Level Dependent Signal Flow In The Light Pupil Reflex, *Biological Cybernetics*, 68, 229–234, 1993.

Krieger, et al., Prognostic And Clinical Relevance Of Pupillary Reponses, Intracranial Pressure Monitoring, And Brainstem Auditory Evoked Potentials In Comatose Patients With Acute Supratentorial Mass Lesions, *Critical Care Medicine*, vol. 21, No. 12, pp. 1944–1950, Dec. 1993.

Chestnut, et al., The Localizing Value Of Assymetry In Pupillary Size In Severe Head Injury: Relation To Lesion Type And Location, *Neurosurgery*vol. 34, No. 5, pp. 840–846, May 1994.

Fairville Medical Options, Inc., Pupilscan II, *Hand–Held, Cordless Pupillometer*, 4 pages, Feb. 12, 1997.

Fairville Medical Options, Inc., Pupilscan II, *Hand–Held, Electronic Pupillometer*, 3 pages.

AMTech GmbH, *Introducing CIP: Compact Integrated Pupillograph and Nystagmograph*, 18 pages, Sep. 1997.

ASL Applied Science Laboratories, Pupilscreen, *Pupilscreen Automatic Self Measurement Pupillometry*, 5 pages.

ASL, *Model 1050, Pupilscan & Pupilscreen*, 5 pages, 1997.

Stark, et al., Top–Down And Bottom–Up Image Processing, *Proceedings of IEEE 1997 International Conference On Neural Networks*, 6 pages, Jun. 1997.

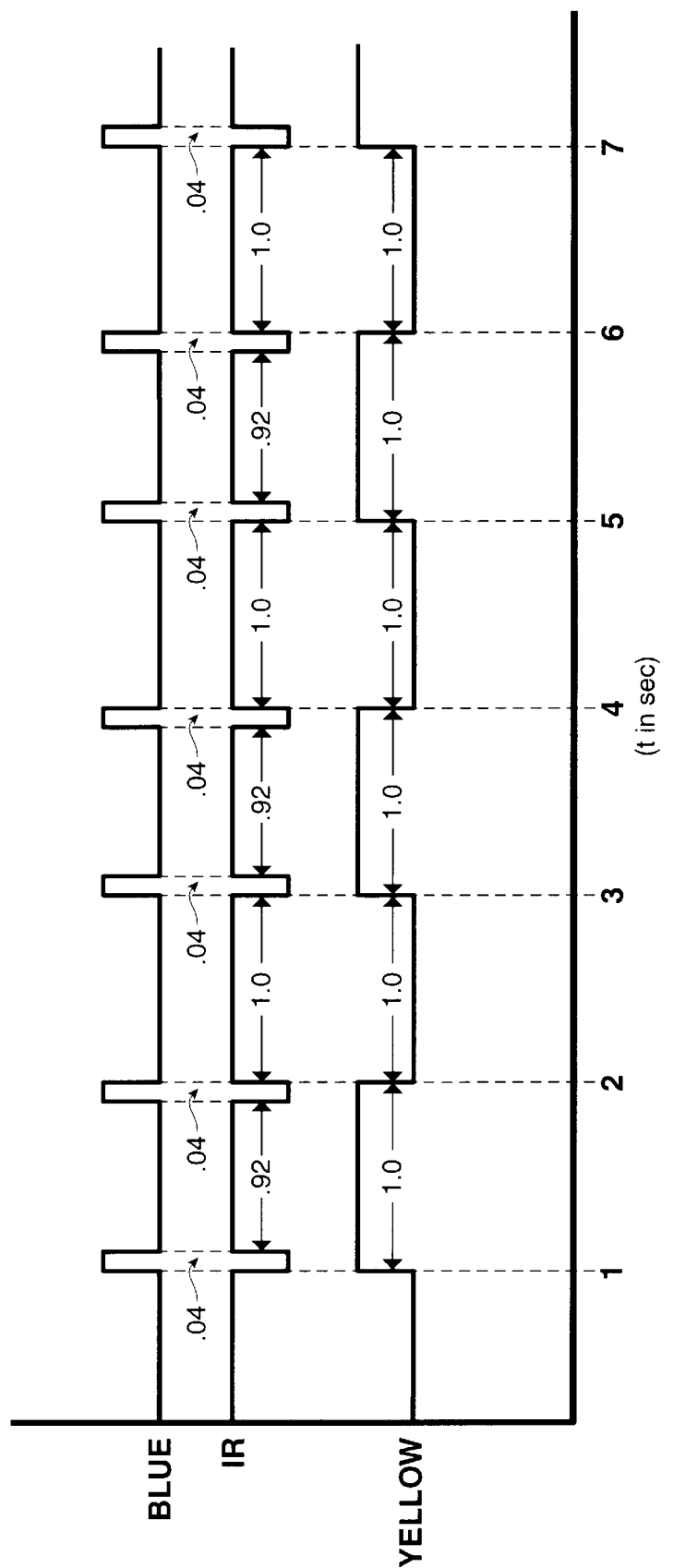

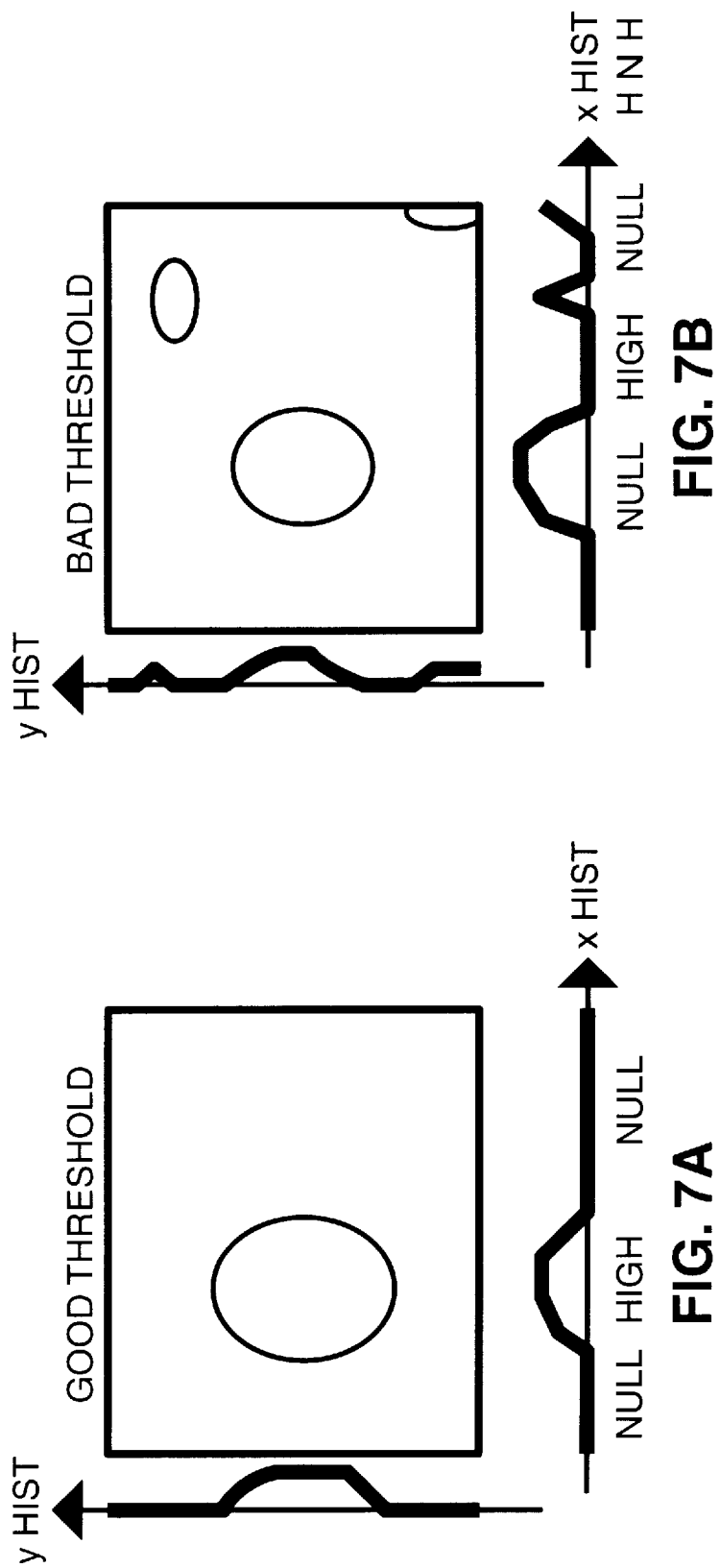

PUPILOMETER WITH PUPIL IRREGULARITY DETECTION CAPABILITY

FIELD OF THE INVENTION

The present invention relates generally to pupilometry systems and, more particularly, to pupilometry systems having a pupil irregularity detection capability. In one particularly innovative aspect, the present invention relates to hand-held pupilometry systems having a pupil irregularity detection capability, to methods and processing sequences used within such systems, and to methods of using such systems.

In another innovative aspect, the present invention relates to a medical diagnostics system incorporating a pupilometer and medical database for correlating actual or derived pupilary image analysis data with stored medical data to formulate medical diagnoses, and to methods of implementing and utilizing such a diagnostics system.

BACKGROUND OF THE INVENTION

Systems for monitoring pupil size and pupil responsiveness characteristics are well known in the art and are generally referred to as pupilometry systems or, simply, pupilometers. One early pupilometer is described in U.S. Pat. No. 3,533,683, which issued to Stark et al. on Oct. 13, 1970 and is entitled "Dynamic Pupilometers Using Television Camera System." The Stark et al. system employed a television camera system, a digital computer system, an infrared light source, and a visual light stimulator for determining the instantaneous size of a pupil as an eye (or neurologic pupilary control system) of a patient was exposed to various stimuli. Like the early Stark et al. system, conventional pupilometers measure, for example, the diameter of a pupil before and after the pupil is exposed to a light stimulus pulse and also measure the rates at which the pupil may constrict and dilate in response to the initiation and termination of the light stimulus pulse. Pupilometers may comprise hand-held units or, alternatively, may comprise desk or table-mounted, stand-alone units. Pupilometers also generally include some mechanism for ensuring that an imager within the pupilometer is properly positioned in relation to a pupil to be imaged. For example, U.S. Pat. No. 5,646,709, issued to Elbert P. Carter, describes an electronic centering system for ensuring that a pupilometer is properly positioned in relation to a pupil to be imaged. Similarly, U.S. Pat. No. 5,187,506, issued to Elbert P. Carter, describes an eye orbit housing for ensuring proper positioning between a pupilometer and an eye of a subject prior to the initiation of a pupilary scanning procedure.

Those skilled in the art will appreciate, however, that for a pupilometer to have maximum utility maximum flexibility should be provided for positioning the imager. For example, in the case of a hand-held system few, if any, restrictions should be placed upon the orientation of the imager prior to enabling an imaging function. The reason for this is that medical personnel at, for example, an accident site may have difficulty in positioning an imager in a prescribed position for acquiring pupilary response data. Thus, it is believed that, for hand-held units in particular, a need exists within the pupilometer field for improved data acquisition and processing systems and methods, as such systems and methods may substantially reduce system dependence on imager orientation and may allow pupilometers to become more user friendly.

Similarly, those skilled in the art will appreciate that a need exists for pupilometers that are capable of evaluating more than a mere pupilary response to light stimulus pulses. For example, it is believed that a substantial need exists for a pupilometer that is capable not only of measuring changes in pupilary diameter in response one or more light stimulus pulses, but also of evaluating pupil shape and/or segmental responses to a visual stimulus. Stated somewhat differently, it is believed that a substantial need exists for a pupilometer having a pupilary shape irregularity or non-uniformity detection capability.

Finally, it is believed that a substantial need exists for pupilometer-based diagnostics systems, as such systems may provide medical practitioners with a cost effective, non-invasive means for gathering and assessing numerous physiologic parameters.

SUMMARY OF THE INVENTION

In one particularly innovative aspect, the present invention is directed toward a pupilometer having a pupil shape irregularity detection capability. For example, a pupilometer in accordance with the present invention may comprise an imaging sensor for generating signals representative of a pupil of an eye, a data processor coupled to the imaging sensor, and a program executable by the data processor for enabling the data processor to process signals received from the imaging sensor and to thereby identify one or more regions of non-uniformity or irregularity within an image of a perimeter of the imaged pupil.

In one presently preferred embodiment, the one or more regions of pupilary non-uniformity or irregularity are identified by identifying a center point of a pupil and determining a plurality of radii representing distances from the center point to the perimeter of the pupil along a respective plurality of angles in a $R, \theta$ coordinate system.

In another innovative aspect, the present invention is directed to a medical diagnostics system incorporating a pupilometer and medical database for correlating actual or derived pupilary image analysis data with stored medical data to formulate medical diagnoses, and to methods of implementing and utilizing such a diagnostics system.

In still other innovative aspects, the present invention is directed to improved thresholding and image data processing algorithms for use within a pupilometer. For example, a pupilometer in accordance with the present invention may utilize a plurality of row and column histogram data sets in an iterative fashion to identify a preferred threshold value for locating the pupil of an eye within an image data frame.

A pupilometer in accordance with the present invention also may process image frame data to determine a shape and/or diameter of the sclera/iris border of an eye and, thereafter, use the determined shape or diameter to evaluate an orientation of the eye of the patient and/or to correlate measured units with defined units of measurement.

Finally, when provided with an additional armature supporting, for example, a visible light emitting diode (LED), a pupilometer in accordance with the present invention may be used to measure afferent or consensual pupilary responses to visual stimulus pulses. In such embodiments, a visual stimulus is applied to an eye under examination, and the response of the monitored pupil is recorded and evaluated. Then, as the monitored pupil is allowed to dilate, a stimulus pulse is applied to the other eye of the patient, to see whether or not the monitored pupil again constricts. Following the second stimulus pulse, the monitored pupil is allowed again to dilate, and a final visual stimulus is applied to the eye under examination. During the final stimulus pulse, the constrictive response of the monitored pupil (or lack thereof) is again measured. By measuring the response of the monitored pupil to each stimulus pulse, it is possible to detect retinal impairment in each eye of the patient.

Other objects and features of the present invention will become apparent from consideration of the following description taken in conjunction with the accompanying drawings.

BRIEF DESCRIPTION OF THE DRAWINGS

FIG. 6 is a timing diagram illustrating a typical stimulus/illumination sequence for the IR, blue and yellow LEDs that may be used within a pupilometer in accordance with the present invention.

FIGS. 7(a) and 7(b) are illustrations of histogram data sets that may be developed in accordance with a preferred thresholding algorithm utilized by a pupilometer in accordance with the present invention.

DESCRIPTION OF PREFERRED EMBODIMENTS

Figure 1:
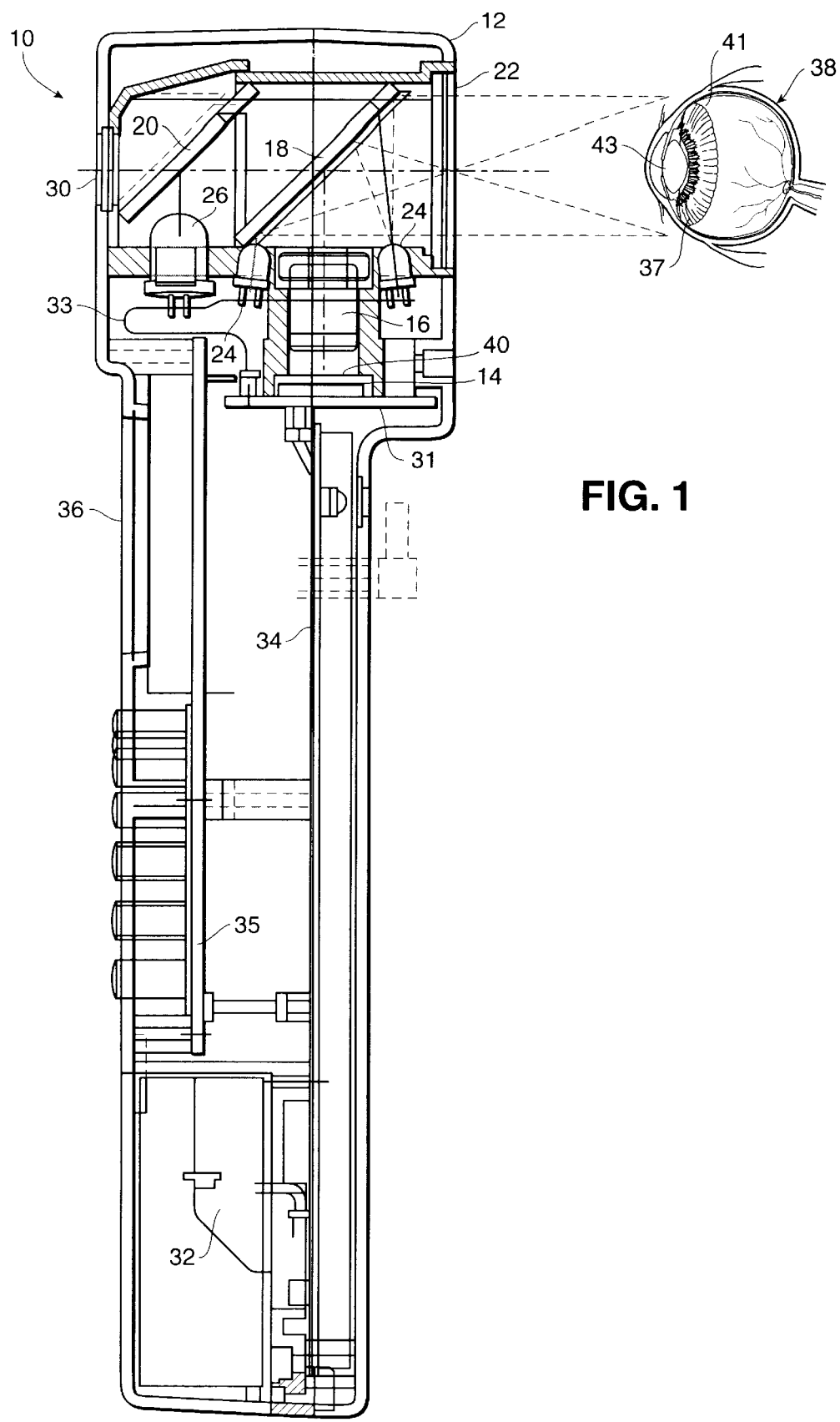
FIG. 1 is a cross-sectional view of a hand-held pupilometer in accordance with a preferred form of the present invention.
Figure 2:
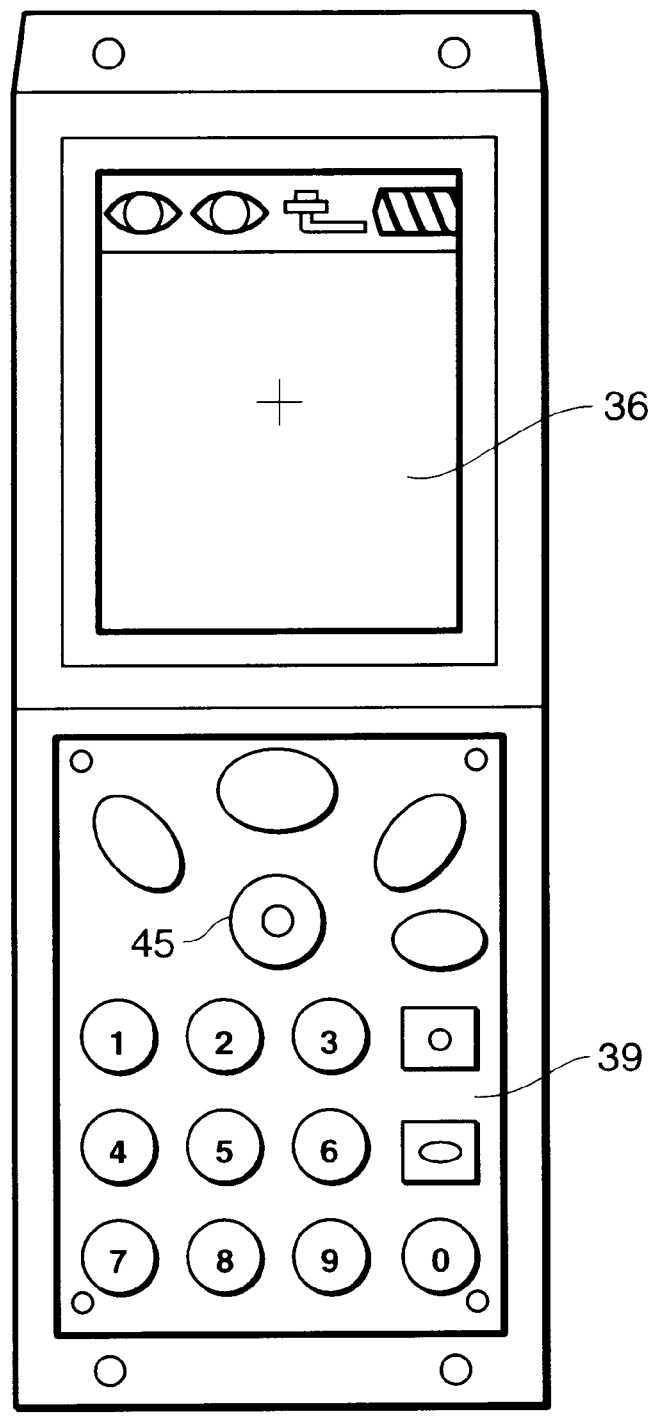
FIG. 2 is an illustration of a liquid crystal display and keypad that may be provided on a hand-held pupilometer in accordance with the present invention.

A. Hardware Components of a Pupilometer in Accordance with the Present Invention Turning now to the drawings, FIG. 1 provides a cross-sectional view of a hand-held pupilometer 10 in accordance with the present invention. FIG. 2 provides an illustration of a liquid crystal display and key pad that may be provided on the hand-held pupilometer 10, and FIG. 3 is an enlarged cross-sectional view of an imaging section of the hand-held pupilometer 10.

Figure 3:
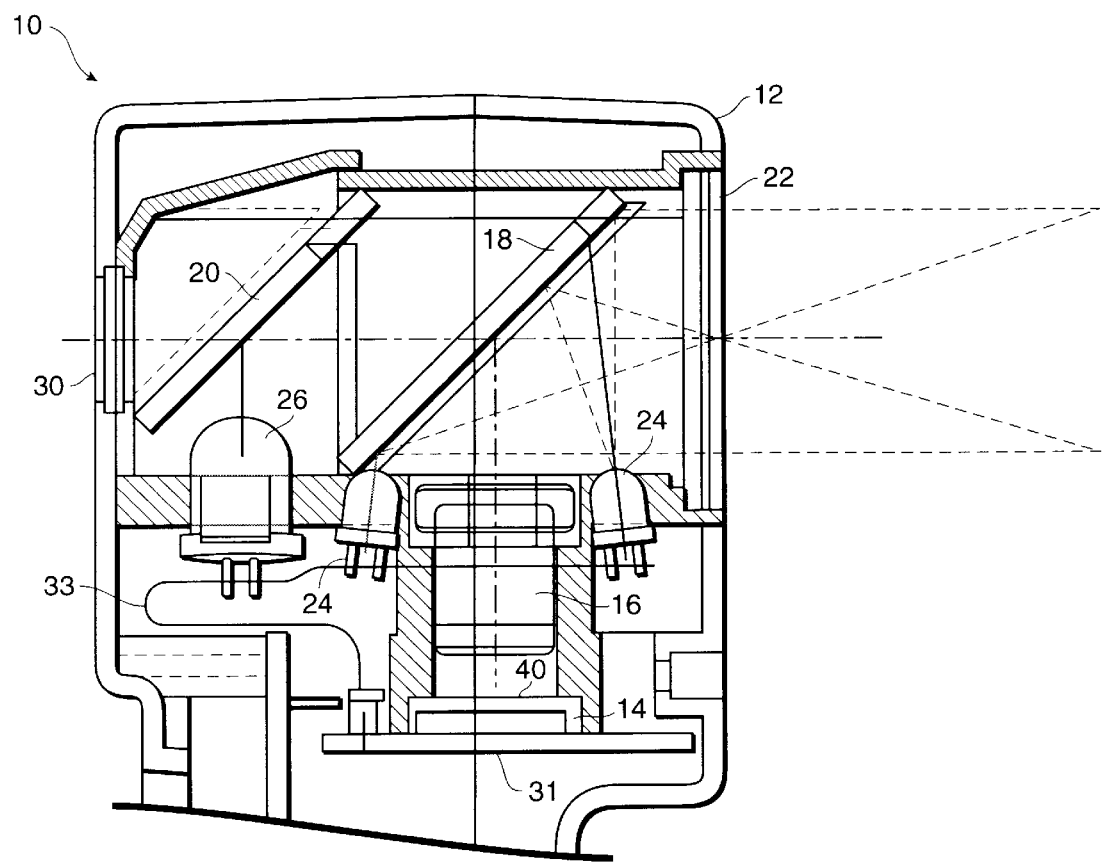
FIG. 3 is an enlarged cross-sectional view of an imaging section of a hand-held pupilometer in accordance with the present invention.

As shown in FIGS. 1–3, the pupilometer 10 preferably includes a housing 12 wherein an imaging sensor 14, an objective lens 16, first and second beam splitters 18 and 20, a shield 22, four infrared (IR) LEDs 24, two yellow LEDs 26, a blue LED 28 (shown in FIG. 4), a reticle 30, a battery 32, an image signal processing board 34 and a liquid crystal display 36 are mounted. Stated somewhat differently, the pupilometer may comprise a viewing port (reticle 30 and shield 22), an imaging system (objective lens 16, imaging sensor 14 and related image processing electronics), an illumination system (IR LEDs 24, blue LED 28 and related control circuitry) and a stimulus system (yellow LEDs 26 and related control circuitry).

1. The Viewing Port

The viewing port (reticle 30 and shield 22) is provided to aid a user in properly positioning the pupilometer 10 for initial data acquisition. By looking through the reticle 30 and shield 22, the user of the pupilometer 10 is able to properly position the pupilometer 10 in front of an eye 38 of a patient, such that an image of the pupil of the patient's eye may be projected onto the imaging sensor 14. The reticle 30 preferably has circular targets (not shown) silk screened or etched on one surface. The targets are positioned along the user's line of sight so as to appear concentric with the iris and pupil of an eye 38 under observation.

Those skilled in the art will appreciate that the reticle 30 and shield 22 also serve as environmental barriers and function to minimize exposure of the imaging system to caustic cleaning agents, biological material and airborne dust, all of which can have a negative impact upon the performance of the imaging system.

2. The Imaging System

The imaging sensor 14 preferably comprises a N×M bit CMOS imaging sensor of a type that is commercially available. One such imaging sensor is the 384×288 bit, Model OV5017, CMOS imaging sensor manufactured and distributed by Omnivision Technologies, Inc. of Sunnyvale, Calif. The imaging sensor 14 is mounted to an imager board 31 of the pupilometer 10 and is coupled to a microprocessor (not shown) provided on a main processing or mother board 34 of the pupilometer 10. This allows for direct capture of digital images. Images in the form of 8 bit (or greater) gray scale bit maps are stored in system memory for image analysis and display on the liquid crystal display 36 (shown in FIG. 2). The microprocessor (not shown) preferably comprises an Elan SC 400 manufactured and distributed by Advanced Micro Devices, Inc., of Austin, Tex.

The imaging system of the present invention is designed such that, when the hand-held pupilometer 10 is positioned in front of the eye 38 of a subject, a properly illuminated and in-focus image of the pupil 43 of the subject's eye 38 is obtained at the sensor plane 40 of the pupilometer 10. The objective lens 16 and a first beam splitter (i.e., wavelength selective filter) 18 preferably are used to focus an image of the pupil 43 of the subject's eye 38 on the sensor plane 40. In a preferred form, the objective lens 16 comprises a five element lens having a focal length of 7.0 mm. The first beam splitter 18 preferably comprises a glass substrate having a thickness of 1.6 mm that is coated with a multi-layer dielectric coating (not shown) to form a wavelength selective filter. The subject side 42 of the beam splitter 18 is coated to enhance reflection at the blue and infrared (IR) wavelength bands with a 45° angle of incidence. The user side 44 of the beam splitter 18 is AR coated to minimize effects resulting from multiple reflections in the image path.

Thus, as shown in FIGS. 1 and 3, the beam splitter 18 functions to direct blue and/or IR light generated by the blue and IR LEDs 28 and 24, respectively, toward the eye 38 of a patient and to provide a return path to the imaging sensor 14 for blue and/or IR light that is reflected from the eye 38 of the patient.

The microprocessor (not shown) provided on the main signal processing board 34 controls the operation and function of the various components comprising the imaging system as described more fully below.

3. The Illumination System

Figure 4:
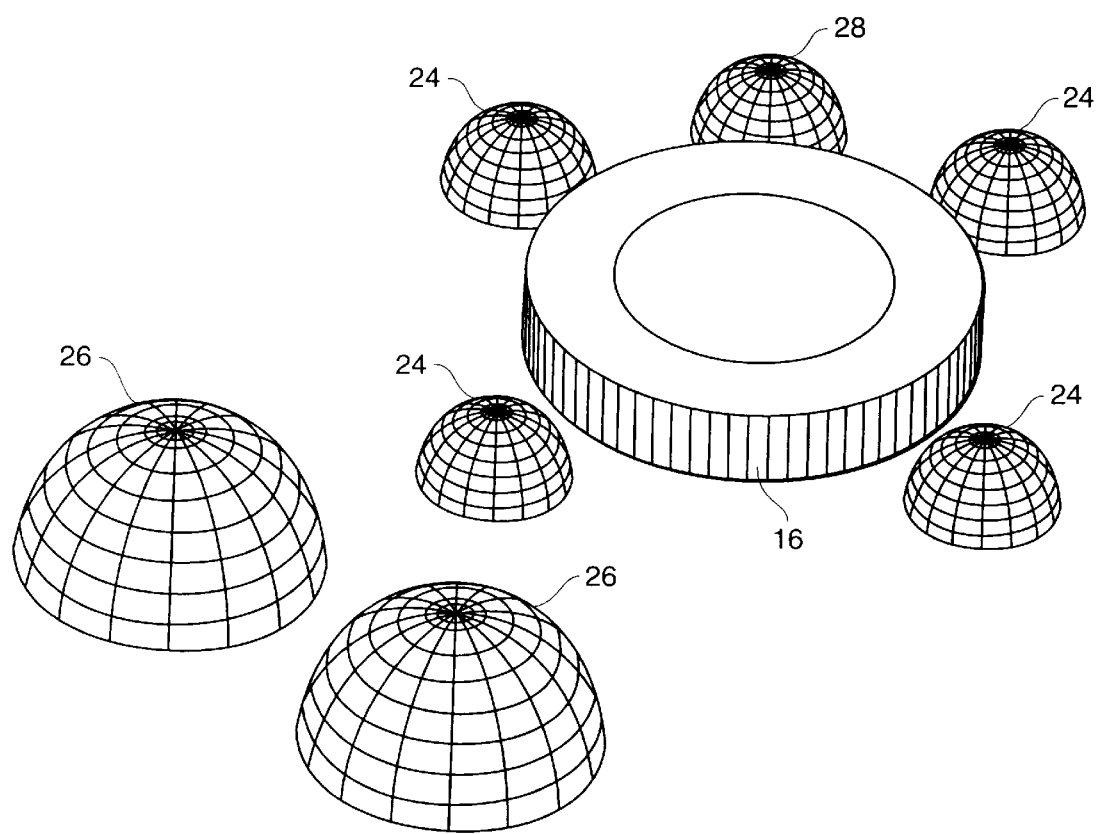
FIG. 4 is a three-dimensional plan view showing a preferred arrangement of a plurality of IR, blue and yellow LEDs that may be used for ocular illumination and stimulation within a pupilometer in accordance with the present invention.

The illumination system preferably comprises a blue light emitting diode (LED) 28 and four infrared (IR) LEDs 24. The IR LEDs 24 preferably are arranged symmetrically about the objective lens 16 of the imaging system. The IR LEDs 24 and blue LED 28 are coupled to a flex circuit 33 that is coupled to the main signal processing board 34. When activated by the microprocessor (not shown), the IR LED's 24 emit IR light preferably having a wavelength of substantially 850 nm. Thus, those skilled in the art will appreciate that the emission bandwidth of the IR LEDs 24 lies beyond the physiological response of the human eye but within the photoelectric response of the imaging sensor 14. Stated somewhat differently, while the human eye is unable to detect the IR light emitted by the IR LEDs 24, IR light generated by the IR LEDs 24 and reflected by the eye 38 of a subject may be detected by the imaging sensor 14. The four IR LEDs 24 preferably are arranged in diametrically opposed groups of two, as shown in FIG. 4. By arranging the IR LEDs 24 in the manner shown in FIG. 4, it is possible to more precisely control the IR illumination of a patient's eye 38 and, moreover, to achieve levels of 0, 50 and 100% illumination, if desired.

The blue LED 28 is used for ocular illumination in situations where the sclera/iris border of a patient's eye 38 may be difficult to detect with IR illumination alone. As shown in FIG. 4, the blue LED 28 preferably is placed on the same radial arc that is defined by the IR LEDs 24, which surround the objective lens 16. The blue LED 28, when activated by the microprocessor (not shown), preferably emits light having a wavelength of substantially 470 nm. It has been discovered by the inventors hereof that light in the blue color band may be used to substantially improve sclera/iris border image contrast because the iris 37 and sclera 41 of a subject's eye 38 generally have substantially different light absorption and reflection characteristics in the blue color band. Thus, the use of a blue LED 28 for sclera/iris border imaging is believed to be a particularly innovative aspect of the present invention.

Because the human eye is responsive to blue radiation, the blue LED 28 preferably is only activated for brief periods of time in relation to the temporal response of a subject's eye 38 or, alternatively, is used in conjunction with the stimulus LEDs 26 described below. Moreover, in a preferred form, IR and blue light illumination of the eye 38 of a subject may be performed in a multiplexed fashion, such that the eye of the subject is illuminated with IR light for a first period of time and, thereafter, illuminated with blue light for a second period of time. This is discussed more fully below with reference to FIG. 6.

The microprocessor (not shown) provided on the main signal processing board 34 controls the operation and function of the various components comprising the illumination system as described more fully below.

4. The Stimulus System

The stimulus system of the pupilometer 10 comprises two yellow LEDs 26 and a second beam splitter 20. The yellow LEDs 26 preferably are coupled to the flex circuit 33 and, when activated by the microprocessor (not shown), emit light having a wavelength of substantially 570 nm. Like the first beam splitter 18, the second beam splitter 20 preferably comprises a glass substrate having a thickness of 1.6 mm and is coated with a multi-layer dielectric coating (not shown) to form a wavelength selective filter. The subject side 50 of the beam splitter 20 is coated to enhance reflection at the yellow wavelength band with a 45° angle of incidence, and the user side 52 of the beam splitter 20 is AR coated to minimize effects resulting from multiple reflections in the user's observation path. The stimulus system of the pupilometer 10 preferably provides on-axis illumination of the pupil 43 of the eye 38 of a patient, as shown in FIG. 1.

B. Software Components of a Pupilometer in Accordance with the Present Invention Turning now to FIGS. 5–7, a pupilometer 10 in accordance with the present invention is a microprocessor based system and, therefore, preferably includes several software components or modules for controlling its operation. As is well know in the art, an operating system provides fundamental machine level interfaces between the hardware elements comprising the pupilometer 10. More specifically, various device drivers are used to provide an interface between the microprocessor (not shown) and the imaging sensor 14, IR LEDs 24, yellow LEDs 26, blue LED 28, keypad 39 and liquid crystal display 36.

The highest level of programming or code used within the pupilometer 10 is referred to herein as the P-Program, and the P-Program preferably is divided into five principal objects corresponding to different hardware and mathematical components. The five principal objects are illustrated in block diagram form in FIG. 5 and preferably include a graphic user interface (GUI) object 100, a stimulus/illumination object 102, a CMOS camera object 104, a feature extraction object 106 and an analysis object 108. All of the above-listed objects preferably are developed in Microsoft Visual C++ and Windows CE, and the graphic user interface (GUI) object 100 preferably is based on Win32 Api functions that are available in Windows CE. Visual C++ and Windows CE are software products distributed by Microsoft Corp. of Redmond, Wash.

1. Graphic User Interface (GUI) Object

The graphic user interface object 100 allows for data/information exchange between a user and the pupilometer 10. Information relating to the current status of the pupilometer 10 including mode of operation (i.e., direct or consensual response, left or right eye measurement etc.) and the battery level is displayed via the graphic user interface object 100. All inputs and outputs of the pupilometer 10 preferably are coordinated via the graphic user interface object 100. Verification of subject ID numbers and/or patient identification data may be accomplished under control of the graphic user interface object 100. Measurement parameters are determined and set with the assistance of the graphic user interface object 100. Instructions during measurement sequences and images of the iris 37 of the eye 38 of a subject are provided on the liquid crystal display 36 under control of the graphic user interface object 100. Similarly, results of measurement sequences are displayed on the liquid crystal display 36 under control of the graphic user interface object 100, and the option to transfer measurement results to a printer or network computer (not shown) is available through the graphic user interface object 100.

2. Stimulus/Illumination Object

The stimulus/illumination object 102 defines and controls the function of the yellow LEDs 26, IR LEDs 24 and blue LED 28 and, therefore, controls the stimulation and illumination of the eye 38 of a subject. The stimulus/illumination object 102 defines the various light profiles (i.e., yellow, IR and blue) as a function of time and controls activation of the yellow, IR and blue LEDs 26, 24 and 28, accordingly. In a typical stimulus/illumination sequence, the LEDs 26, 24 and 28 preferably are activated in the manner described below. However, those skilled in the art will appreciate that the stimulus/illumination sequence may be varied depending upon the circumstances of any given situation, and that variations in the stimulus/illumination sequence may be effected through the user interface object 100.

During a typical stimulus/illumination sequence, the LEDs 24, 26 and 28 may be operated as shown in FIG. 6. For example, during a typical measurement sequence, the yellow LEDs 26 may be activated and deactivated for successive 1 second intervals (i.e., "on" for 1 second and "off" for 1 second) for a period of 10 seconds total. Simultaneously, the IR LEDs 24 may be activated for all periods when the yellow LEDs 26 are "off," and may be deactivated, activated and deactivated (i.e., turned "off," "on" and "off") for respective 0.04, 0.92 and 0.04 second intervals, while the yellow LEDs 26 are turned "on." Similarly, the blue LED 28 may be activated, deactivated and activated for respective 0.04, 0.92 and 0.04 second intervals, while the yellow LEDs 26 are turned "on," and may be deactivated during all periods when the yellow LEDs are turned "off." This allows for the operation of the IR LEDs 24 and blue LED 28 to be multiplexed. In such an embodiment, the image frame transfer rate preferably would be set, for example, to 50 frames per second.

3. The CMOS Camera Object

The CMOS camera object 104 controls the transfer of image data frames between the CMOS imaging sensor 14 and memory associated with the microprocessor (not shown) provided on the main signal processing board 34 (i.e., between the imaging sensor 14 and the P-Program). Preferably, the rate of image frame transfer between the imaging sensor 14 and the memory associated with the microprocessor (not shown) may be programmably set within a range from 1 frame per second to 50 frames per second, depending upon the needs and/or desires of the user. However, those skilled in the art will appreciate that in some instances it may be desirable to provide for faster frame transfer rates, and that such rates might be as high or higher than 100 frames per second. The image frame acquisition or transfer rate is defined by the user under control of the graphic user interface object 100.

4. The Feature Extraction Object

The feature extraction object 106 defines several image processing procedures that are used to isolate a pupil within an image and to extract several pupil features such as size, shape and position from each pupil image data frame. All processing procedures defined by the feature extraction object preferably are performed on each image data frame, with the exception of the automatic thresholding procedure described below. The automatic thresholding procedure is applied during an initial calibration phase and, therefore, does not need to be applied to each image data frame. Rather, the results of the automatic thresholding procedure are used during feature extraction processing for each image data frame. The results of the automatic thresholding procedure also may be used to set and/or adjust image exposure gain settings within the system.

The feature extraction object 106 employs a flying spot processing algorithm to identify the center of the pupil, a fitted circumference and/or radius of the pupil and, preferably, 48 radii representing the distance between the center and perimeter of the pupil at 48 separate angles in an R,θ coordinate system, where θ defines an angular orientation about the center of the pupil, and R represents the radius of the pupil at that orientation. The fitted radius of the pupil is determined by selecting a circumference that best fits a contour of the pupil and by solving the equation 2πr to obtain the radius value (r).

Those skilled in the art will appreciate that, by defining and evaluating 48 distinct radii about the center of the pupil, it is possible in accordance with the present invention to detect one or more non-uniformities or irregularities that may exist around the perimeter of the pupil. It also is possible to characterize the shape of the pupil as circular, elliptical etc. based upon the determined radii. It also is possible to evaluate selected sections of a pupil perimeter to determine whether or not those sections exhibit normal contour characteristics and/or normal responses to visual stimulus. It is believed that these capabilities represent significant improvements over conventional pupilometry systems, as these features allow not only for the performance of conventional pupil aperture and response evaluations, but also for the performance of pupil shape and sectional contour evaluations. Thus, where a particular affliction may produce a defined irregularity in pupil shape or defined sectional response to visual stimulus, the affliction may be identified through the use of a pupilometer in accordance with the present invention.

The inputs to, and outputs obtained from, the flying spot algorithm may be defined as follows:

Input Parameters:

Frame=eye image frame generated by the CMOS imaging sensor 14

Threshold=gray level threshold value; any pixel having a gray scale value greater than the threshold value is considered to be part of the pupil.

Output Parameters:

Output=fitted radius and center of pupil, 48 radii.

It is assumed herein that within the gray scale used by the pupilometer 10 the color black will be associated with a high gray scale value, such as 255, and the color white will be associated with a low gray scale value, such as 0. However, those skilled in the art will appreciate that the relative maximum and minimum values could be reversed.

It is believed that the use of flying spot algorithms are well known in the art and, therefore, that the flying spot algorithm need not be described in detail herein. Nonetheless, the basic flying spot procedure may be described as follows. The flying spot procedure starts with a large circumference centered on the image of an eye and iteratively reduces the size of the circumference. In reducing the size of the circumference and adjusting the center location of the circumference, for each iteration the following momentums will be computed:

$$\mu x = 1/N * \sum_{x,y} gray\_level\_sign(x, y)(x - x0)$$

$$\mu y = 1/N * \sum_{x,y} gray\_level\_sign(x, y)(y - y0)$$

$$\mu r = 1/N \sum_{x,y} gray\_level\_sign(x, y)$$

where N represents the number of pixels having coordinates x,y in the circumference contour; gray_level_sign(x,y) is +1, if the gray level value of the pixel (x,y) is greater than the threshold value; gray_level_sign(x,y) is −1, if the gray level value of the pixel (x,y) is less than the threshold value; and x0,y0 are the center coordinates of the circumference.

The x and y coordinates of the circumference center and the radius are updated as follows:

$$x0 = x0 + \mu x * Gain\_x$$

$$y0 = y0 + \mu y * Gain\_y$$

$$radius = radius + \mu r * Gain\_r.$$

As indicated above, the updating procedure is applied iteratively, each time calculating the momentum and then changing the center and radius of the flying spot, such that the circumference finally converges to a circumference that best fits the contour of the pupil.

Once the fitted radius and center of the pupil are determined, 48 radii representing the distance between the center and perimeter of the pupil at 48 separate angles in an R,θ coordinate system preferably are determined, where θ defines an angular orientation about the center of a pupil, and R represents the radius of the pupil at that orientation. By evaluating the 48 determined radii, it is possible to characterize the overall shape of the pupil and to determine whether or not any sectional non-uniformities or irregularities are present about the perimeter of the pupil. Such processing may be performed either by the feature extraction object 106 or the analysis object 108.

Another principal function performed by the feature extraction object is thresholding. The thresholding function automatically identifies a gray level value that separates the pupil from the background in an image data frame. Moreover, when an appropriate threshold value is determined, all pixels having a gray level value greater than the threshold value are considered to comprise part of the image of the pupil, and all pixels having a gray level value less than the threshold are considered to correspond to background.

Preferably, the defined threshold value represents the average of a maximum hypothetical threshold value and a minimum hypothetical threshold value. The maximum and minimum hypothetical threshold values are derived through respective histogram analysis routines. Moreover, as shown in FIGS. 7(*a*) and 7(*b*), for each hypothetical threshold value two histograms are evaluated, one for the rows of pixels within an image frame, and one for the columns of pixels within the image frame. The histogram value for a given row or column is determined by counting the pixel locations in that row or column that have a gray level value that exceeds the hypothetical threshold level. Thus, the number of values within a histogram preferably corresponds to the number of rows or columns in the image data frame, and each value represents the number of pixels in the specific row or column that have a gray level exceeding the hypothetical threshold value.

Turning now in particular to FIGS. 7(*a*) and 7(*b*) the hypothetical maximum and hypothetical minimum threshold values are determined by iteratively altering a hypothetical threshold value until a prescribed histogram profile is achieved. An acceptable profile is illustrated in FIG. 7(*a*) and is one in which a null-high-null pattern is achieved for both a row histogram (y Hist) and column histogram (x Hist). More specifically, an acceptable profile preferably comprises a single "high" bordered by a pair of "nulls." Unacceptable profiles are illustrated, for example, in FIG. 7(*b*).

The hypothetical maximum threshold value is determined by selecting an absolute maximum value and iteratively decreasing that value and deriving corresponding histogram data sets until acceptable row and column histogram profiles are achieved. Similarly, the hypothetical minimum threshold value is determined by selecting an absolute minimum value and iteratively increasing that value and deriving corresponding histogram data sets until acceptable row and column histogram profiles are achieved. Once the hypothetical maximum and minimum threshold values are determined, those values are averaged to determine the defined threshold value that will be used by the feature extraction object 106. Those skilled in the art will appreciate that the defined threshold value may correspond to the maximum hypothetical threshold value, the minimum hypothetical threshold value, or any value that is between those values. Thus, in alternative embodiments, the defined threshold value could be determined, for example, based on a weighted average of the maximum and minimum hypothetical threshold values. In such an embodiment, the defined threshold value may comprise a value corresponding to the sum of the minimum hypothetical threshold value and $\frac{2}{3}$ of the difference between the maximum and minimum hypothetical threshold values.

5. The Analysis Object

The analysis object 108 analyzes the configuration characteristics of a pupil as a function of time. Preferably, the analysis object 108 receives, as inputs, from the feature extraction object 106 a plurality of data sets for each captured image data frame. The data sets preferably include the time of image capture in msec, x and y coordinates of the pupil center, radius of the flying spot circumference, 48 radii representing the distance between the center and border of the pupil for 48 selected angles within an R,θ coordinate system, and an applied stimulus record for the relevant entry. Upon receiving the input data sets, the analysis object 108 preferably derives at least the following information from the data sets: minimum pupil aperture, maximum pupil aperture, difference between maximum and minimum pupil apertures, latency of pupil response to yellow light stimulus, pupil constriction velocity, first and second pupil dilation velocities and, if desired, pupil irregularity magnitude and location information. Where pupil irregularities are detected, the location of the irregularity preferably is identified by its θ coordinate. However, graphical indications also may be provided on the display 36 of the pupilometer 10.

Further, in alternative embodiments, the analysis object 108 may include programming for effecting a multi-varied analysis wherein a plurality of selected variables including, for example, latency indicia, constriction velocity indicia, first and second dilation velocity indicia, segmental static and/or dynamic analysis indicia, constriction/dilation velocity ratio indicia, and maximum and minimum diameter indicia are evaluated for one or both eyes of a patient to arrive at one or more scalar values that are indicative of an overall physiologic or pathologic condition of the patient or, alternatively, to arrive at one or more scalar values that are indicative of an overall opto-neurologic condition of the patient.

With regard to the information derived by the analysis object 108, the maximum pupil aperture, minimum pupil aperture and difference determinations require the identification of the maximum pupil aperture and minimum pupil aperture within a set of image data frames and, thereafter, computation of the difference between those values. The latency determination provides an indication in milliseconds of the time that it takes for a pupil to begin to respond to a visible (i.e., yellow) light stimulus pulse. Further, those skilled in the art will appreciate that, when a pupil is exposed to a visual light stimulus pulse, the pupil generally will, after some latency period, constrict and, once the stimulus is discontinued, dilate and return to its original size and configuration. Thus, the analysis object 108 evaluates the response of a pupil to a visual stimulus to determine a pupil constriction velocity and evaluates the response of the pupil to termination of the stimulus to determine first and second dilation velocities. First and second dilation velocities are evaluated because a pupil generally will dilate quickly for a first period of time and, thereafter, will dilate more slowly until its original size and configuration are achieved. Finally, as explained above, an analysis object 108 in accordance with the present invention also preferably identifies any irregularities in the shape of the pupil. Such irregularities may be either static or dynamic in nature. For example, a static irregularity may take the form of an irregular pupil shape in ambient light, whereas a dynamic irregularity may take the form of increased latency for a particular section of the pupil during a response to a the initiation or termination of a visual stimulus. With regard to static irregularities, such irregularities may be identified by identifying the angular orientations of radii that do not fall within prescribed limits, differ from other calculated radii by a predetermined deviation or differ from the fitted radius by a predetermined amount, deviation or percentage.

Finally, an analysis object 108 in accordance with the present invention preferably includes programming for identifying statistical anomalies within derived results. This allows an analysis object 108 in accordance with the present invention to discard either actual pupilary response data sets (i.e., fitted radius, center and radii calculations) or derived data sets (i.e., max aperture, min aperture, latency, constriction rate or dilation rates) when a selected value differs from other values by a statistically significant degree. When such anomalies are identified, the relevant data sets are not included in averaging functions, and where many anomalies are identified, an imaging sequence will be invalidated and must be repeated.

C. Operation of a Pupilometer in Accordance with the Present Invention

Turning now to FIG. 8, operation of a pupilometer 10 in accordance with the present invention proceeds as follows. Generally the pupilometer 10 will be configured according to a default mode of operation. The default mode defines a set of values for basic operation of the device. The defined values may include, for example, values for scan duration, illumination duration and/or profile, stimulus duration and/ or profile and stimulus intensity level. However, it will be appreciated that all of the above-listed values may be programmably set under control of the graphic user interface object 100. Thus, it will be appreciated that default programming values generally will be utilized by the pupilometer 10 absent entry of an override by the user in a scan sequence program mode.

A typical image acquisition and analysis procedure may proceed as follows. If the pupilometer 10 has been idle for a predetermined period of time (e.g., 120 seconds), the pupilometer 10 is automatically placed in a battery-conserving sleep mode (step 202). By depressing the "scan" button 45 (shown in FIG. 2), the user causes the pupilometer 10 to enter a "ready" mode (step 200). At this time, the user is prompted to enter an alphanumeric subject or patient identification number via the keypad 39 or to download any necessary patient information from a network computer via an infrared data interface, such as an IrDA interface that is provided on numerous conventional personal computer products (step 204). Once any requisite patient identification data has been entered into the system, the user is prompted via the liquid crystal display 36 or an audio prompt to hold down the "scan" button 45 and to position the pupilometer 10 in front of the eye 38 of a subject (step 210).

When the user depresses the "scan" button 45, the microprocessor (not shown) initiates an imaging test sequence. The yellow LEDs 26 preferably are not activated during the test sequence. During the test sequence the images that are acquired by the imaging sensor 14 may be displayed on the liquid crystal display (LCD) 36. Preferably, the P-program analyzes the image data frames that are acquired during the test sequence, determines whether or not the pupilometer 10 is properly positioned for obtaining measurements, and determines if all necessary parameters are met to ensure high-quality data recovery. If the test criteria are not met, the user is prompted to reposition the pupilometer 10. After any requisite test criteria are met, the P-program will continue to run the test sequence until the "scan" button 45 is released.

Once the scan button 45 is released, the P-program preferably will initiate a prescribed measurement sequence and will activate the illumination system of the pupilometer 10 as needed during the measurement sequence. Upon completion of the measurement sequence, the user is informed via the LCD 36 or an audio prompt that the measurement sequence has been completed (steps 226–228).

Following completion of the measurement sequence, the P-program preferably will analyze the image data frames that have been obtained and will display the results of the analysis on the LCD 36. If the results are satisfactory (i.e., are statistically sound), the user may then be prompted to download the results to a printer or related network via the IrDA interface (not shown) (step 246). If the results are not satisfactory, the user is prompted to repeat the measurement sequence (step 222).

Figure 9:
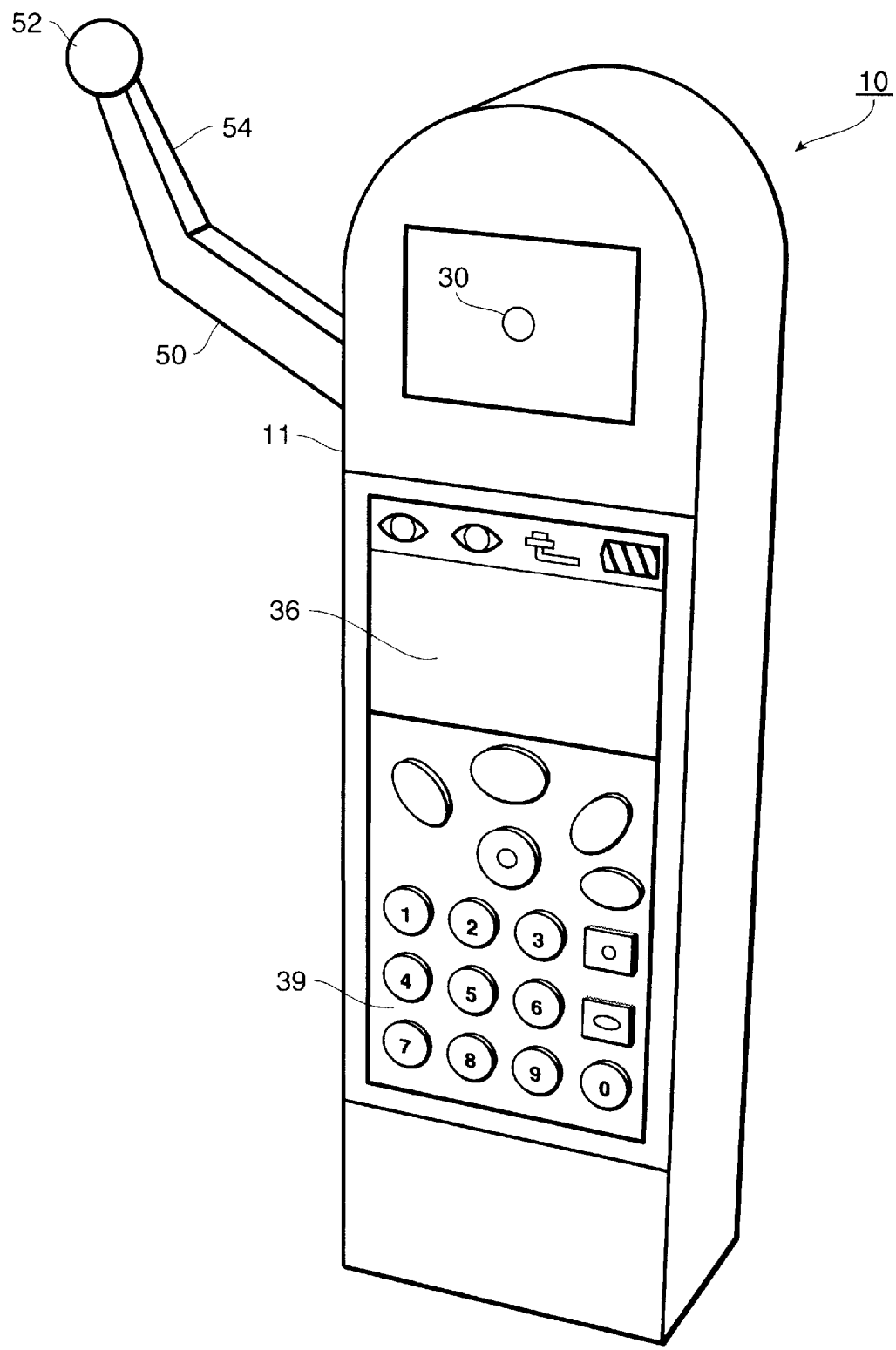
FIG. 9 is an illustration of a pupilometer incorporating a consensual measurement attachment in accordance with the present invention.

Finally, after an initial set of measurement are obtained, the user may be prompted for a decision to measure the pupilary characteristics of the other eye of the subject/patient, or the user may be prompted for a decision to make a consensual response measurement (steps 238, 242). The consensual response measurement may take the form of a "swinging flashlight" measurement discussed more fully below. If a consensual measurement is to be performed, the user may be prompted to couple a consensual measurement attachment (shown in FIG. 9) to the pupilometer and to position a yellow LED 52 mounted on the attachment in front of the appropriate eye of the subject/patient. If the consensual measurement attachment is permanently affixed to the pupilometer 10, the user may only need to deploy and/or properly position the attachment.

D. Incorporation of Consensual Measurement Apparatus in a Pupilometer in Accordance with the Present Invention Turning now to FIG. 9, a pupilometer 10 in accordance with the present invention may incorporate a consensual measurement apparatus or armature 50 to enable consensual pupilary responses to be analyzed. In a preferred embodiment, the armature 50 may detachably engage a main body 11 of the pupilometer 10. However, as explained above, the armature 50 also may be permanently affixed to the main body 11 of the pupilometer 10.

One test for analyzing consensual pupilary responses is commonly referred to within the medical community as a "swinging flashlight test." During a typical swinging flashlight test one eye of a subject is monitored, and a visible light stimulus is applied first to the eye of the patient that is being monitored, then to the eye of the patient that is not monitored and, finally, again to the eye that is monitored. If the eyes of the patient are normal, the pupil of the monitored eye should constrict in response to all of the light stimulus pulses (regardless of which eye the stimulus pulse is applied to). Following application of the first light stimulus, the pupil of the monitored eye should begin to dilate, and upon application of the second light stimulus (i.e., upon application of stimulus to the non-monitored eye), the pupil of the monitored eye should again constrict. If the monitored pupil does not respond adequately to the second stimulus pulse, it may be inferred that the retina of the non-monitored eye somehow may be impaired. If the monitored pupil does not respond adequately to the third stimulus pulse, it may be inferred that the retina of the monitored eye somehow may be impaired.

By using a consensual measurement attachment 50 in accordance with the present invention, it is possible to perform a "swinging flashlight" test using the pupilometer 10. For example, the when performing a "swinging flashlight" test, the P-program may first cause the yellow LEDs 26 within the pupilometer 10 to be activated for a period of, for example, 1 second. The P-program then may deactivate the yellow LEDs 26, and 0.5 second following deactivation of the yellow LEDs 26 may activate for 0.5 second the yellow LED 52 located at the distal end 54 of the consensual attachment. Finally, after deactivating the yellow LED 52 and waiting for a period of, for example, 0.5 second, the P-program may again activate the yellow LEDs 26 for a period of 1 second. Image frames may be obtained by the imaging sensor 14 at a rate of, for example, 10 frames per second and for a total period of 5.0 or more seconds to evaluate the consensual response of the imaged eye. If desired, the process may be repeated a predetermined number of times.

E. Miscellaneous System Calibration and Pupil Identification Processing Techniques In alternative embodiments, the P-program of a pupilometer 10 in accordance with the present invention may incorporate a calibration algorithm that uses acquired data descriptive of the perimeter of the iris 37 of the eye 38 of a patient to define a relationship between pixel spacing data and real world measurement parameters and/or to evaluate an orientation of a patient's eye 38 in relation to the pupilometer 10.

For example, in one innovative aspect, the P-program of a pupilometer 10 may cause the iris of the eye of a patient to be illuminated by blue light (i.e., may activate the blue LED 28) and, while the patient's eye is so illuminated, may obtain an image of the sclera/iris border of the patient's eye. A flying spot or similar processing algorithm may then be used to identify a best fitting elliptical circumference for the sclera/iris border of the patient's eye, and the radii or horizontal and vertical diameters of the circumference may be compared to or correlated with assumed sclera/iris border radii or diameters to provide a correlation between a pixel count and a real world measurement. For example, if the horizontal diameter of a sclera/iris border is assumed to be 11.7 mm, and the sclera/iris border measures 117 pixels in diameter, the P-program of the pupilometer 10 may derive a pixel measurement to real world correlation factor of 10 pixels/mm, and that correlation factor may be used to provide the user with pupil measurement information. In accordance with one preferred form of the present invention, the horizontal diameter of the sclera/iris border is assumed to be 11.75 mm for in all subjects. However, those skilled in the art will appreciate that a different diameter, such as 11.0 mm or 12.0 mm, may also be assumed.

Similarly, by evaluating the shape of the sclera/iris border of an eye it is possible to estimate the angular orientation of the eye with respect to the pupilometer 10 and, moreover, to evaluate the orientation of an eye with relation to a vertical axis of the eye. Preferably, this may be done by evaluating a degree of ellipticity of the imaged sclera/iris border and assuming that the shape of the sclera/iris border has a predetermined elliptical shape. Such, measurements may be further refined by comparing the shape of a pupil to the shape of a surrounding sclera/iris border to determine whether variations in the shape of a pupil arise from angular orientation of the eye in relation to the pupilometer 10, or from non-uniformities or irregularities in the perimeter of the pupil.

In another innovative aspect, a pupilometer 10 in accordance with the present invention may include software for utilizing physical landmarks to assist in locating a pupil within an image data frame. In such an embodiment, the feature extraction object 106 of the P-program executed by the microprocessor (not shown) may include code for identifying characteristic structures of ocular tissue such as eyelids and/or eyelashes within an image data frame, and for using the location of those structures to predict the location of a pupil within the image data frame. Additional landmarks that may be located in accordance with the present invention include the lachrymal punctum, lachrymal caruncula, and lateral and medial papebral commisures of a patient's eye. These landmarks also may be used to identify which eye of a patient is being monitored.

F. Diagnostics Systems and Methods in Accordance with the Present Invention

In still another innovative aspect, the present invention is directed to improved diagnostics systems and methods incorporating a pupilometer 10 and medical database (not shown). For example, it is contemplated in accordance with the present invention that data representative of a plurality of pupilary response or configuration characteristics associated with one or more physical or pathological conditions may be stored within a medical diagnostics data base, that a pupilometer 10 may be used to obtain data descriptive of one or more pupilary response or configuration characteristics from a patient, and that the obtained data may be compared to the stored data within a data analysis system to identify one or more physiologic or pathologic characteristics or conditions of the patient. Further, in a preferred form, the obtained and/or stored pupil configuration data may be descriptive of one or more static or dynamic regional non-uniformities that may exist within the perimeter of a patient's pupil.

While the invention is susceptible to various modifications and alternative forms, specific examples thereof have been shown by way of example in the drawings and are herein described in detail. It should be understood, however, that the invention is not to be limited to the particular forms or methods disclosed, but to the contrary, the invention is to cover all modifications, equivalents, and alternatives falling within the spirit and scope of the appended claims.

What is claimed is:

1. A pupilometer comprising:
   a CMOS sensor for generating image data representative of a pupil of a patient; and
   deformation detection means coupled to said CMOS sensor for identifying one or more selected regions within an image of a perimeter of said pupil that exhibit a predetermined amount of regional distortion.

2. A pupilometer comprising:
   a microprocessor;
   a memory coupled to said microprocessor;
   an imaging device coupled to said microprocessor;
   a visible light source coupled to said microprocessor;
   an IR light source coupled to said microprocessor; and
   a display coupled to said microprocessor;
   said memory having stored therein a program for enabling said microprocessor to cause a plurality of visible light stimulus pulses to be generated by said visible light source, to cause said IR light source to generate IR light for illuminating a pupil, to enable said imaging device to acquire a plurality of images of said illuminated pupil, to process data sets representative of said images of said illuminated pupil to obtain information descriptive of a response of said pupil to said visible light stimulus pulses, and to cause said information to be depicted on said display;

said information descriptive of a response of said pupil to said visible light stimulus pulses comprising information indicative of a degree of non-uniform deformation of a selected segment of a perimeter of said pupil.

3. A handheld pupilometer comprising:

a housing having a display, microprocessor, memory, imaging device, visible light source and IR light source mounted therein;

said microprocessor being electronically coupled to said display, said memory, said imaging device, said visible light source and said IR light source; and said memory having stored therein a program for enabling said microprocessor to cause at least one visible light stimulus pulse to be generated by said visible light source, to cause said IR light source to generate IR light for illuminating a pupil, to enable said imaging device to acquire a plurality of images of said illuminated pupil, and to process a plurality of data sets representative of said plurality of images of said illuminated pupil to obtain information descriptive of a response of said pupil to said at least one visible light stimulus pulse, and to cause said information to be depicted on said display;

said information descriptive of a response of said pupil to said at least one visible light stimulus pulse comprising information indicative of a degree of deformation of a selected segment of a perimeter of said pupil.

4. The handheld pupilometer of claim 3, wherein said information descriptive of a response of said pupil to said at least one visible light stimulus pulse comprises information descriptive of a dynamic response of said selected segment of said perimeter of said pupil.

5. The pupilometer of claim 3, wherein said imaging device comprises a CMOS N×M sensor.

6. The pupilometer of claim 3, wherein said imaging device comprises a CCD camera.

7. The pupilometer of claim 3 further comprising means coupled to said microprocessor for downloading to a remote storage device said information descriptive of a response of said pupil to said at least one visible light stimulus pulse.

8. The pupilometer of claim 7 wherein said means for downloading comprises at least one of either an IR transmitter circuit or a RF transmitter circuit.

9. The pupilometer of claim 7 wherein said means for downloading comprises at least one of either a data port or a modem for coupling said pupilometer to a computer.

10. The pupilometer of claim 9, wherein said means for acquiring image data comprises a source of infrared light, a source of visible light and an imaging device under microprocessor control.

11. The pupilometer of claim 10, wherein said imaging device is selected from a group consisting of a CCD camera and a N×M CMOS imaging sensor.

12. A handheld pupilometer comprising:

a housing having mounted therein means for acquiring image data representative of ocular tissue, means for processing said image data, and means for displaying information derived from said image data, said means for processing said image data comprising a microprocessor and programming for determining a pixel brightness threshold value, programming for locating a pupil within a plurality of image data sets using said pixel brightness threshold value, and programming for identifying one or more regions around a perimeter of said pupil that exhibit a non-uniform change in shape when said pupil is exposed to illumination of a predetermined type.

13. The pupilometer of claim 10, wherein said means for acquiring image data comprises a source of infrared light, a source of visible light and an imaging device under micrprocessor control.

14. The pupilometer of claim 12, wherein said illumination comprises exposure to ambient light.

15. A method for correlating pupilary responses with pathological indications, said method comprising the steps of:

storing within a database data representative of a plurality of pupilary response characteristics associated with one or more pathological indications;

using a pupilometer obtaining pupilary response data from a patient, said pupilary response data being representative of one or more pupilary response characteristics of said patient; and comparing within a data analysis system said pupilary response data obtained from said patient with said data representative of a plurality of pupilary response characteristics to identify one or more pathological conditions of said patient.

16. A method for correlating pupilary measurements with pathological indications, said method comprising the steps of:

storing within a database data representative of a plurality of pupilary configurations and associated pathological conditions;

using a pupilometer obtaining pupilary configuration data from a patient; and comparing within a data analysis system said pupilary configuration data obtained from said patient with said data representative of said plurality of pupilary configurations to identify one or more pathological conditions of said patient.

17. The method of claim 16, wherein said pupilary configuration data comprises data descriptive of a pupilary response to at least one visible light stimulus pulse.

18. The method of claim 16, wherein said pupilary configuration data comprises data descriptive of a pupilary change in shape responsive to at least one light stimulus pulse.

19. The method of claim 16, wherein said pupilary configuration data comprises data descriptive of a pupilary response to ambient light exposure.

20. A method for correlating pupilary responses with pathological indications, said method comprising the steps of:

storing within a database data representative of a plurality of pupilary sectional configurations and associated pathological conditions;

using a pupilometer obtaining pupilary configuration data from a patient, said pupilary configuration data including data indicative of selected regional non-uniformities of a pupil of said patient if said patient's pupil exhibits such regional non-uniformities; and comparing within a data analysis system said pupilary configuration data obtained from said patient with said data representative of said plurality of pupilary sectional configurations to identify one or more pathological conditions of said patient.

21. A method for correlating pupilary responses with a scalar value indicative of a state of health of an individual or physiological system of said individual, said method comprising the steps of:

storing within a database data representative of a plurality of pupilary response characteristics associated with one or more pathological indications;

using a pupilometer obtaining pupilary response data from a patient, said pupilary response data being representative of one or more pupilary response characteristics of said patient; and comparing within a data analysis system said pupilary response data obtained from said patient with said data representative of said plurality of pupilary response characteristics to derive said scalar value.

22. A system for use in diagnosing pathological conditions, said system comprising:

a pupilometer for obtaining data descriptive of one or more pupilary characteristics from a patient;

a database for storing data descriptive of a plurality of pupilary characteristics and associated physical conditions; and a central processing unit coupled to said digital pupilometer and said database for comparing said data obtained by said pupilometer to said data stored within said database such that a pathological condition of said patient may be diagnosed based upon said comparison.

23. The system of claim 22 further comprising a processing subroutine for generating a scalar indicator based upon a result of said step of comparing said data stored within said pupilometer to said data stored within said database.

24. The system of claim 22 further comprising a display coupled to said central processing unit for displaying images of said patient's pupil and for providing an indication of whether or not said pupilary characteristics of said patient correspond to any of said pupilary characteristics represented by said data stored within said database.

25. A method for locating a pupil within an image of ocular tissue, said method comprising the steps of:

establishing a pixel brightness threshold value for discriminating between light and dark gray scale data comprising said image, and comparing gray scale image data at a plurality of pixel locations within said image of ocular tissue to said pixel brightness threshold value to identify a region within said image of ocular tissue that represents said pupil, wherein said step of establishing a pixel brightness threshold value comprises the steps of selecting a pixel brightness threshold value, constructing vertical and horizontal histogram data sets from said image of ocular tissue, wherein each histogram data set comprises a plot of sums of pixel locations having a value exceeding said threshold value along respective rows or columns of pixels comprising said image, determining whether curves mapped from said vertical and horizontal histogram data sets comprise at least one maximum value bordered by a pair of null values, and repeating said selecting, constructing and determining steps until a pixel brightness threshold value is identified that satisfies said determining step.

26. The method of claim 25, wherein said step of selecting a pixel brightness threshold value comprises the steps of selecting a maximum pixel brightness threshold value and decreasing said pixel brightness threshold value in increments from said maximum pixel brightness threshold value upon each repetition of said selecting step.

27. The method of claim 25, wherein said step of selecting a pixel brightness threshold value comprises the steps of selecting a minimum pixel brightness threshold value and increasing said pixel brightness threshold value in increments from said minimum pixel brightness threshold value upon each repetition of said selecting step.

28. The method of claim 27, wherein said assigning step comprises the step of deriving a pixel brightness threshold value comprising the sum of the relative minimum pixel brightness threshold value and $\frac{2}{3}$ times the difference between the relative maximum and relative minimum pixel brightness threshold values.

29. The method of claim 25, wherein said step of selecting a pixel brightness threshold value comprises the steps of selecting a maximum pixel brightness threshold value and decreasing said pixel brightness threshold value in increments from said maximum pixel brightness threshold value until a first predetermined histogram plot is achieved and a relative maximum pixel brightness threshold value is identified, selecting a minimum pixel brightness threshold value and increasing said pixel brightness threshold value in increments from said minimum pixel brightness threshold value until a second predetermined histogram plot is achieved and a relative minimum pixel brightness threshold value is identified, and assigning said pixel brightness threshold value a level between said relative maximum pixel brightness threshold value and said relative minimum pixel brightness threshold value.

30. A method of processing data representative of an image of ocular tissue, said method comprising the steps of:

generating digital image data representative of said image of said ocular tissue;

processing said digital image data representative of said image of said ocular tissue to locate one or more landmarks within said image of said ocular tissue;

using said one or more landmarks determine whether a right eye or left eye of a patient is being monitored.

31. A method of calibrating a pupilometer comprising the steps of:

acquiring at least one data set representative of an image of an eye including a pupil and an iris, deriving from said at least one data set information descriptive of a shape of an outer perimeter region of said iris, deriving from said at least one data set information descriptive of a shape of a perimeter region of said pupil, and comparing said information descriptive of said shape of said outer perimeter region of said iris to said information descriptive of said perimeter region of said pupil to normalize and establish a frame of reference for said information descriptive of said shape of said pupil.

32. A method for calibrating a pupilometer comprising the steps of:

acquiring at least one data set representative of an image of an eye including a pupil and an iris, deriving from said at least one data set an indication of a diameter of an outer perimeter of said iris, comparing said indication of said diameter of said outer perimeter of said iris to an assumed diameter of said iris, and utilizing a difference between said indication of said diameter of said outer perimeter of said iris and said assumed diameter to calibrate said pupilometer.

33. The method of claim 32, wherein said assumed diameter of said iris is a horizontal diameter and is approximately 11.75 mm.

34. A method for calibrating a pupilometer comprising the steps of:

illuminating a portion of an eye including an iris and a pupil with low intensity blue light, using an imaging sensor, obtaining data descriptive of an image of said portion of said eye illuminated by said low intensity blue light, analyzing said data to identify an outer perimeter of said iris of said eye within said image, and using said identified outer perimeter of said iris of said eye to calibrate said pupilometer.

35. A method for acquiring pupilometry data, said method comprising the steps of:

exposing an eye of a patient to blue light pulses and IR pulses in a predetermined sequence, obtaining data descriptive of a shape of an iris of said eye when said eye is exposed to said blue light pulses, and obtaining data descriptive of a shape of a pupil of said eye when said eye is exposed to said IR pulses.

36. The method of claim 35, wherein said light pulses and IR pulses, and said respective data obtaining steps, are multiplexed.

37. A method of calibrating a pupilometer, said method comprising the steps of:

exposing an eye to a plurality of light stimulus pulses, using said pupilometer obtaining a plurality of image data sets representative of respective pupilary responses of said eye to said light stimulus pulses, using said plurality of obtained image data sets deriving response curves representative of said respective pupilary responses, and using said response curves to evaluate a degree of adaptation of said eye to said stimulus pulses.

38. The method of claim 37 further comprising the step of using an estimate of said degree of accommodation of said eye to said stimulus pulses to normalize one or more image data sets representing a pupilary response to a selected stimulus pulse.

39. A pupilometry system comprising:

a display, microprocessor, memory, imaging device, first and second visible light sources and an IR light source;

said microprocessor being electronically coupled to said display, said memory, said imaging device, said visible light sources and said IR light source; and said memory having stored therein a program including stimulus control code for enabling said microprocessor to cause said first visible light source to generate a first visible light stimulus pulse for illuminating a first eye, to cause said second visible light source to generate a second visible light stimulus pulse for illuminating a second eye at a predetermined time following termination of said first visible light stimulus pulse, and to cause said first visible light source to generate a third visible light stimulus pulse for illuminating said first eye at a predetermined time following termination of said second visual light stimulus pulse; including illumination control code for enabling said microprocessor to cause said IR light source to generate IR light for illuminating a pupil of said first eye during a duration of said first, second and third visible light stimulus pulses; including image acquisition code for enabling said microprocessor to cause said imaging device to acquire a plurality of images of said IR illuminated pupil; including image analysis code for enabling said microprocessor to process data sets representative of said images of said IR illuminated pupil to obtain information descriptive of a response of said pupil to said visible light illumination of said first eye and said second eye; and display code for enabling said microprocessor to cause said information to be depicted on said display.

40. The pupilometer of claim 39 further comprising an armature that extends from a main body of said pupilometer for supporting said second visible light source.

41. The pupilometer of claim 40, wherein said armature detachably engages said main body of said pupilometer.

* * * * *

UNITED STATES PATENT AND TRADEMARK OFFICE
CERTIFICATE OF CORRECTION

PATENT NO.    : 6,116,736
DATED         : September 12, 2000
INVENTOR(S)   : Stark et al.

Figure 8A:
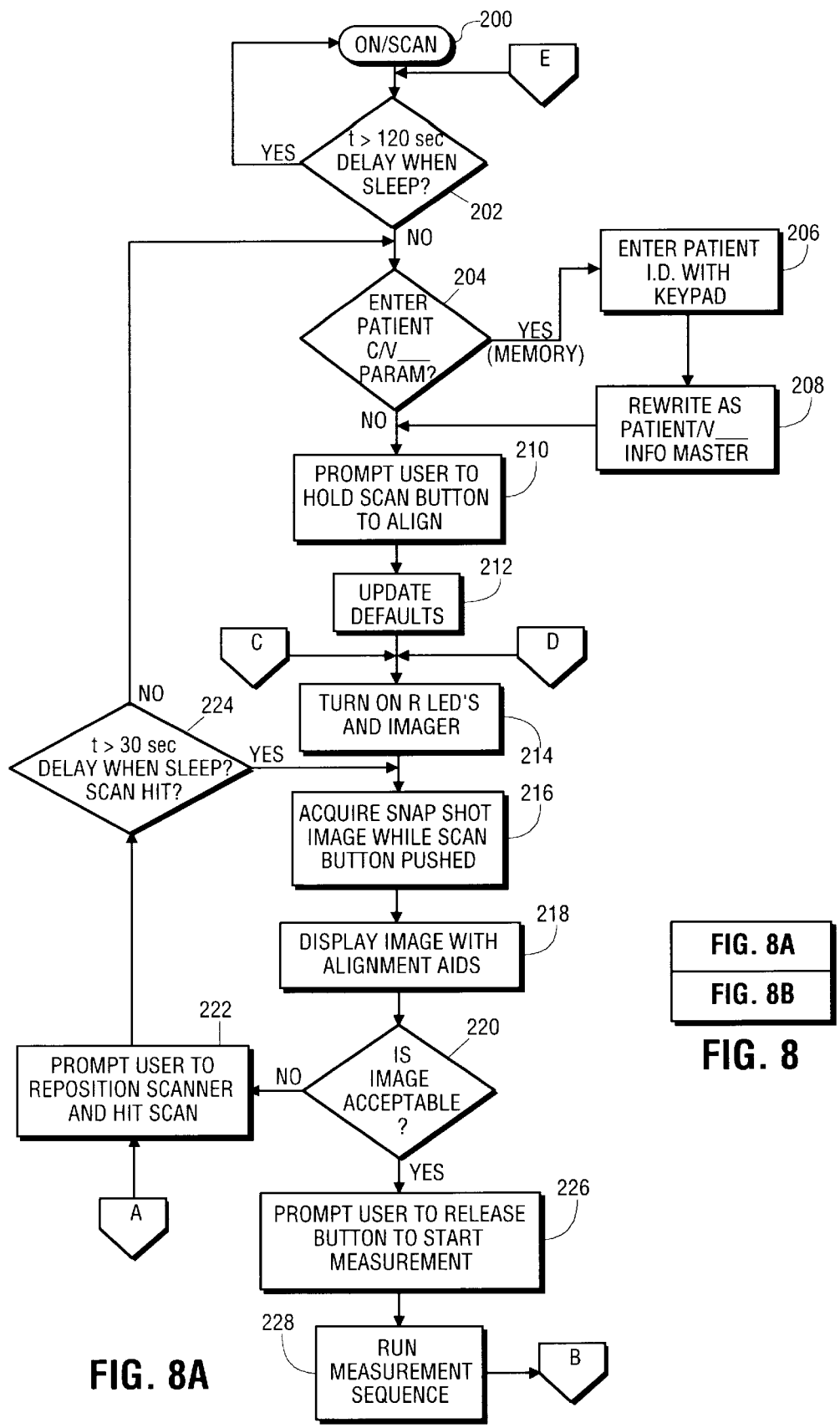
FIG. 8 is a flow chart illustrating a basic operating protocol for a pupilometer in accordance with the present invention.
Figure 8B:
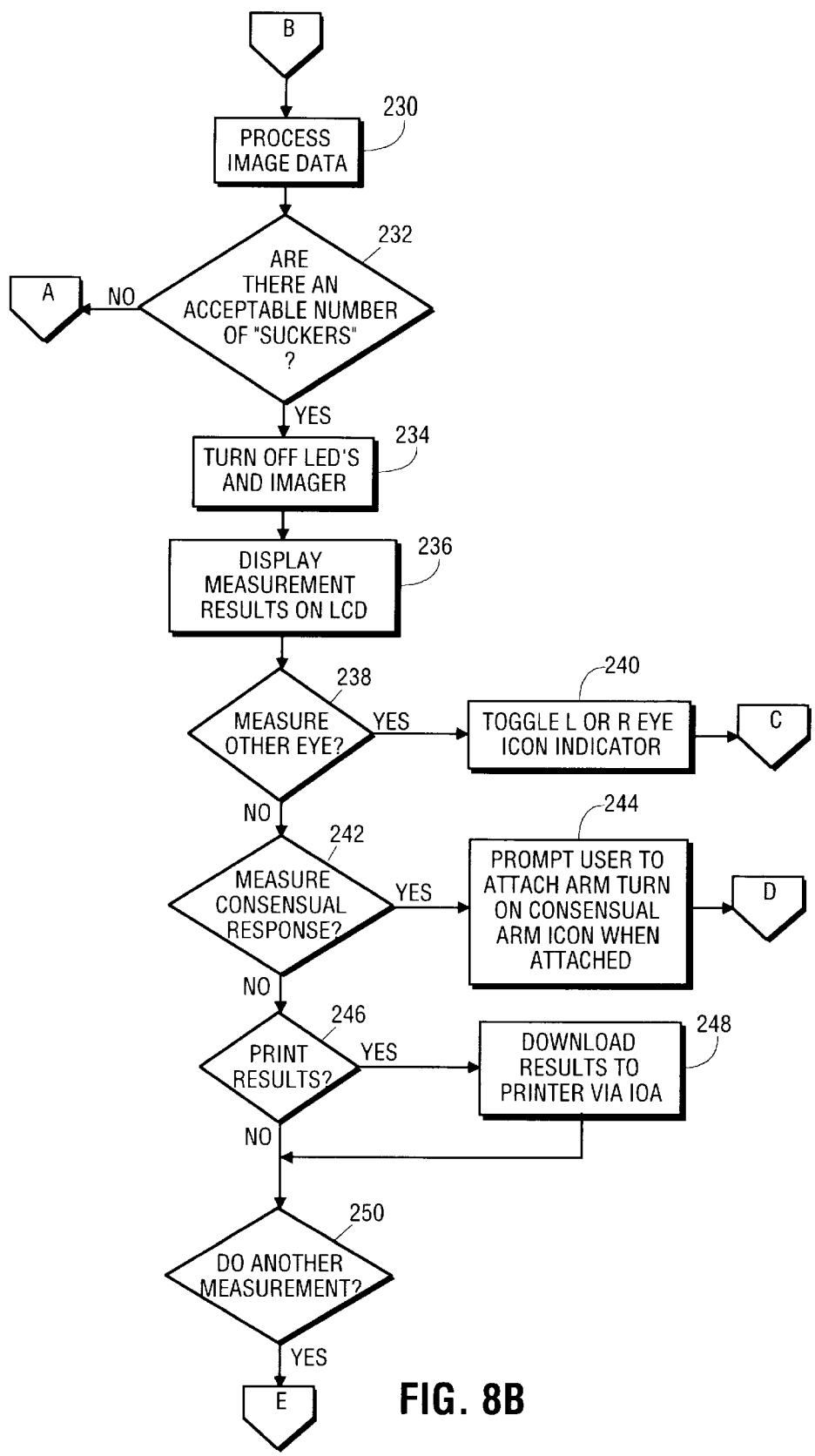

It is certified that error appears in the above-identified patent and that said Letters Patent is hereby corrected as shown below:

Column 3,
Line 36, after "FIG. 8", please insert -- (FIGS. 8A and 8B) --.

Figure 5:
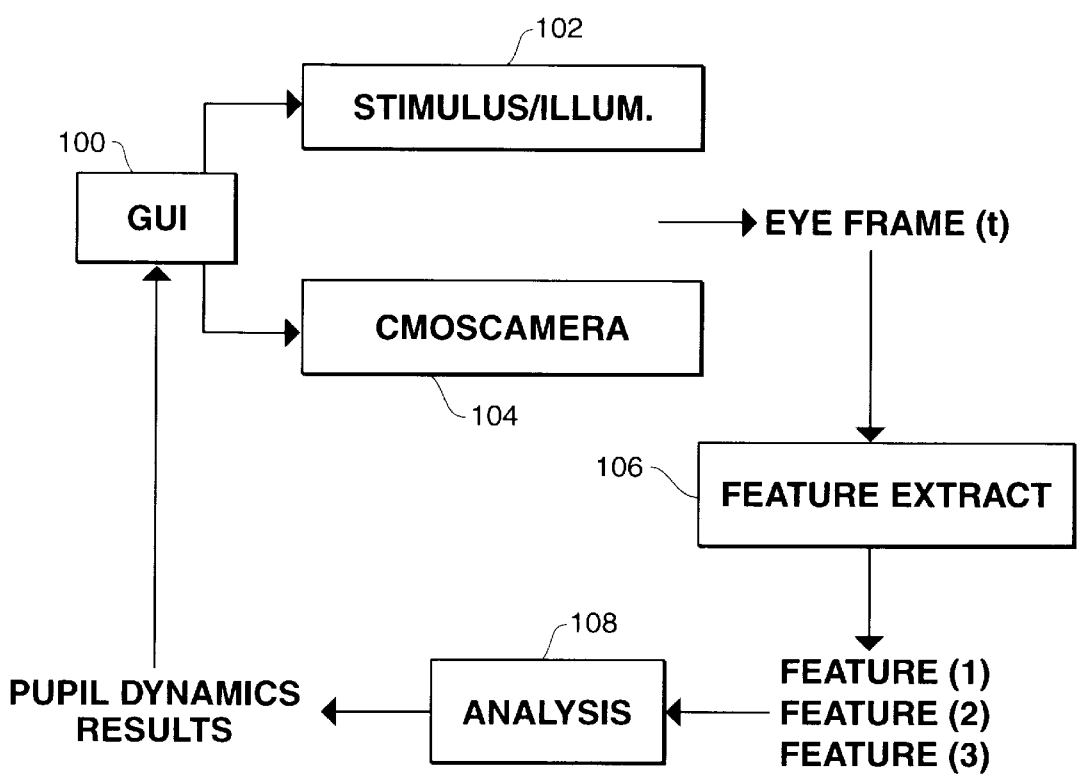
FIG. 5 is a block diagram illustrating a group of programming objects that preferably comprise an operating program of a pupilometer in accordance with the present invention.

Column 6,
Line 3, please change "FIGS. 5-7" to -- FIGS. 5-7b --.
Line 65, please insert -- graphic -- before "user".

Column 18,
Line 32, please insert -- and -- after "tissue;".
Line 33, please change "landmarks determine" to -- landmarks to determine --.

Signed and Sealed this

Twenty-eighth Day of May, 2002

*Attest:*

*Attesting Officer*

JAMES E. ROGAN
*Director of the United States Patent and Trademark Office*